(12) United States Patent
Kim et al.

(10) Patent No.: US 8,554,487 B2
(45) Date of Patent: Oct. 8, 2013

(54) METHOD AND APPARATUS FOR ANALYZING GENOTYPE DATA

(75) Inventors: Ki-eun Kim, Seoul (KR); Kyung-Hee Park, Seoul (KR); Jung-joo Hwang, Suwon-si (KR); Jae-Heup Kim, Hwaseong-si (KR); Yeon-Su Lee, Goyang-si (KR); Kyusang Lee, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 1632 days.

(21) Appl. No.: 11/326,164

(22) Filed: Jan. 4, 2006

(65) Prior Publication Data
US 2006/0252059 A1 Nov. 9, 2006

(30) Foreign Application Priority Data
Jan. 4, 2005 (KR) ........................ 10-2005-0000382

(51) Int. Cl.
*G01N 33/50* (2006.01)
(52) U.S. Cl.
USPC ........................................................ 702/19
(58) Field of Classification Search
None
See application file for complete search history.

(56) References Cited

U.S. PATENT DOCUMENTS 7,272,506 B2 * 9/2007 Glanowski et al. ............. 702/20
2003/0165869 A1 9/2003 Glanowski et al.

FOREIGN PATENT DOCUMENTS

JP 2004-078371 A 3/2004

OTHER PUBLICATIONS

Japanese Office Action issued on Jan. 25, 2011 for Application No. 2005-380088.

* cited by examiner

*Primary Examiner* — Jason Sims
(74) *Attorney, Agent, or Firm* — Cantor Colburn LLP (57) ABSTRACT

Provided are a method and apparatus for analyzing genotype data plotted in a two-dimensional space. The method includes: connecting points representing the genotype data to a predetermined point to form straight lines and obtaining angles between adjacent straight lines; extracting the two largest angles from the obtained angles; and analyzing the plotted genotype data using three groups of the genotype data separated by the two extracted largest angles. According to the present invention, when the experimental results of classifying genotype are to be analyzed, the two largest angles from the angles obtained by connecting straight lines between points representing each of the genotype data and a predetermined point plotted in a two-dimensional space are detected, and three data regions separated by the detected two largest angles are used to analyze the genotype data. Thus, a large amount of the experimental data for classifying the genotype can be analyzed rapidly and conveniently.

9 Claims, 6 Drawing Sheets

METHOD AND APPARATUS FOR ANALYZING GENOTYPE DATA

This application claims the benefit of Korean Patent Application No. 10-2005-0000382, filed on Jan. 4, 2005, in the Korean Intellectual Property Office, the disclosure of which is incorporated herein in its entirety by reference.

BACKGROUND OF THE INVENTION

1. Field of the Invention

The present invention relates to a method and apparatus for analyzing genotype data plotted in a two-dimensional space, and more particularly, to a method and apparatus for analyzing genotype data in which the two largest angles obtained by connecting straight lines between points representing the genotype data and a predetermined point plotted in a two-dimensional space are detected and three data regions separated by the detected two angles are used to analyze the experimental results of classifying the genotype data.

2. Description of the Related Art

A genotype refers to the genetic makeup that determines a specific characteristic or trait of an organism and is classified into homozygote 1 expressed as A1A1, heterozygote expressed as A1A2, and homozygote 2 expressed as A2A2.

Genotype classification is widely used in doctors' prescriptions for diseases or predictions of diseases, etc., since the classified genotype contains much information about characteristics of physical and psychologic factor, etc. of individuals. However, in order to classify genotype data using data obtained from organisms such as humans, a large amount of experimental data must be analyzed, and thus, the analysis of the data requires much time and is complicated. Further, a basis on whether the classification of genotype data is correct is not clear, and thus, judgments on the experimental results can vary for each observer who analyzes the experimental data.

SUMMARY OF THE INVENTION

The present invention provides a method and apparatus for analyzing genotype data, in which the two largest angles obtained by connecting straight lines between points representing genotype data and a predetermined point plotted in a two-dimensional space are determined and three data regions separated by the detected two angles are used to analyze the experimental results of classifying the genotype data.

According to an aspect of the present invention, there is provided a method of analyzing genotype data plotted in a two-dimensional space, including: connecting points representing the genotype data to a predetermined point to form straight lines and obtaining angles between adjacent straight lines; extracting the two largest angles from the obtained angles; and analyzing the plotted genotype data using three groups of the genotype data separated by the two extracted largest angles.

The obtaining of the angles between the adjacent straight lines may include: obtaining angles between the straight lines and a predetermined straight line and arranging the obtained angles in a decreasing order; and calculating differences between the adjacent angles.

The genotype data plotted in the two-dimensional space may be represented with different colors according to the genotype represented.

The method may include: detecting the genotype data in each of the groups represented with a color other than the color representing the genotype data associated with the group; obtaining the coordinates and number of the detected genotype data; and analyzing the detected genotype data by using the coordinates and number of the detected genotype data.

In the analyzing of the plotted genotype data, if at least one of the two extracted largest angles is less than a first predetermined angle, the genotype classification of the plotted genotype data may be judged to be incorrect.

In the analyzing of the plotted genotype data, if an angle formed by the center group among the three groups is greater than a second predetermined angle, the genotype classification of the plotted genotype data may be judged to be incorrect.

The analyzing of the plotted genotype data may include: if at least one of the two extracted largest angles is less than a first predetermined angle, judging that the experiment for determining the genotype data should be repeated; if the two extracted largest angles are greater than the first predetermined angle and the colors of the genotype data contained in each of the groups are identical, judging that genotype classification of the plotted genotype data is correct; and if the two extracted largest angles are greater than the first predetermined angle and the colors of the genotype data contained in each of the groups are different from each other, judging that a review of the experiment of determining the genotype data is required.

The analyzing of the plotted genotype data may include: if the two largest angles are greater than a first predetermined angle, judging that genotype classification of the genotype data is correct; if the two largest angles are less than the first predetermined angle and an angle of the center group among the three groups is greater than a second predetermined angle, judging that the experiment for determining the genotype data should be repeated; and if the two largest angles are less than the first predetermined angle and the angle of the center group among the three groups is less than the second predetermined angle, judging that a review of the experiment of determining genotype data is required.

The method may include displaying the results of analyzing the genotype data or reclassifying the genotype of the genotype data using the results of analyzing the genotype data.

According to another aspect of the present invention, there is provided an apparatus for analyzing genotype data plotted in a two-dimensional space, including: a straight line extraction unit extracting straight lines connecting points representing the genotype data to a predetermined point; an angle calculation unit obtaining angles between the adjacent straight lines; an angle extraction unit extracting the two largest angles from the obtained angles; and an analysis unit analyzing the plotted genotype data using three groups of the genotype data separated by the two extracted largest angles.

Each of the genotypes of the genotype data plotted in the two-dimensional space may be represented with a different color.

The apparatus may further include: an unclassified data detection unit detecting genotype data in each of the groups represented with a color other than the color representing the genotype data associated with the group; a unclassified data identification unit obtaining the coordinates and number of the detected genotype data; and a unclassified data analysis unit for analyzing the detected genotype data by using the obtained coordinates and number.

If the two extracted largest angles are less than a first predetermined angle, the analysis unit may judge that the genotype classification of the plotted genotype data is incorrect.

If an angle of the center group among the three groups is greater than a second predetermined angle, the analysis unit may judge that the genotype classification of the plotted genotype data is incorrect.

If the colors of the genotype data contained in each of the three groups are different from each other, the analysis unit may judge that the genotype classification of the plotted genotype data is incorrect.

The apparatus may further include a display unit displaying the results of analyzing the genotype data or a classification unit reclassifying the genotype of the genotype data using the results of analyzing the genotype data.

According to another aspect of the present invention, there is provided a computer-readable recording medium having recorded thereon a program for executing the method described above in a computer.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, a method and apparatus for analyzing genotype data according to embodiments of the present invention will be described in more detail with reference to the attached drawings.

Figure 1:
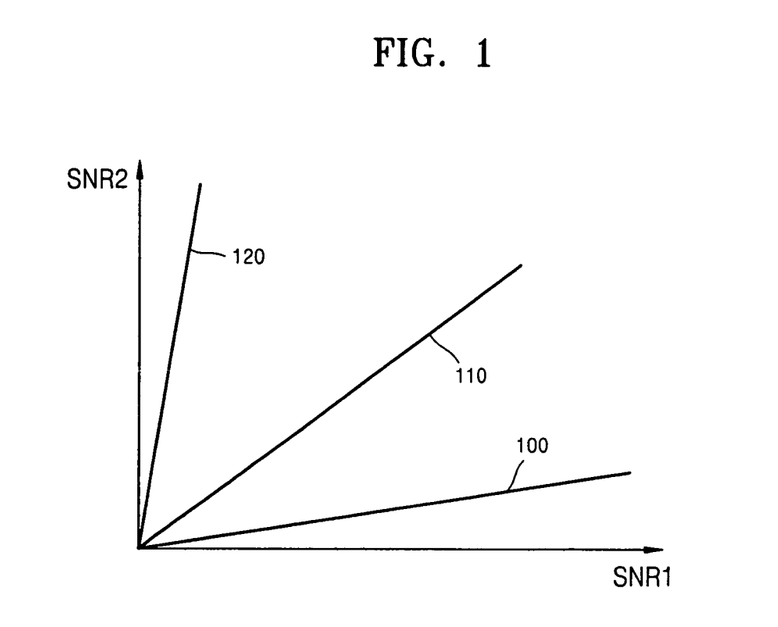
FIG. 1 is a graph illustrating genotype data plotted in a two-dimensional space.

FIG. 1 is a graph illustrating genotype data plotted in a two-dimensional space in which a first signal-to-noise ratio (SNR)1 indicating a distribution of A1 in the experimental data and an SNR2 indicating a distribution of A2 in the experimental data are calculated and plotted. In the case of homozygote 1 expressed by A1A1, the amount of A1 is very large and SNR1 is much greater than SNR2, and thus, the genotype data expressed by A1A1 are plotted on straight line 100. In the case of heterozygote expressed by A1A2, the amount of A1 is nearly the same as the amount of A2 and SNR1 is nearly the same as SNR2, and thus, the genotype data expressed by A1A2 are plotted on straight line 110. In the case of homozygote 2 expressed by A2A2, the amount of A2 is very large and SNR2 is much greater than SNR1, and thus, the genotype data expressed by A2A2 are plotted on straight line 120.

Figure 2:
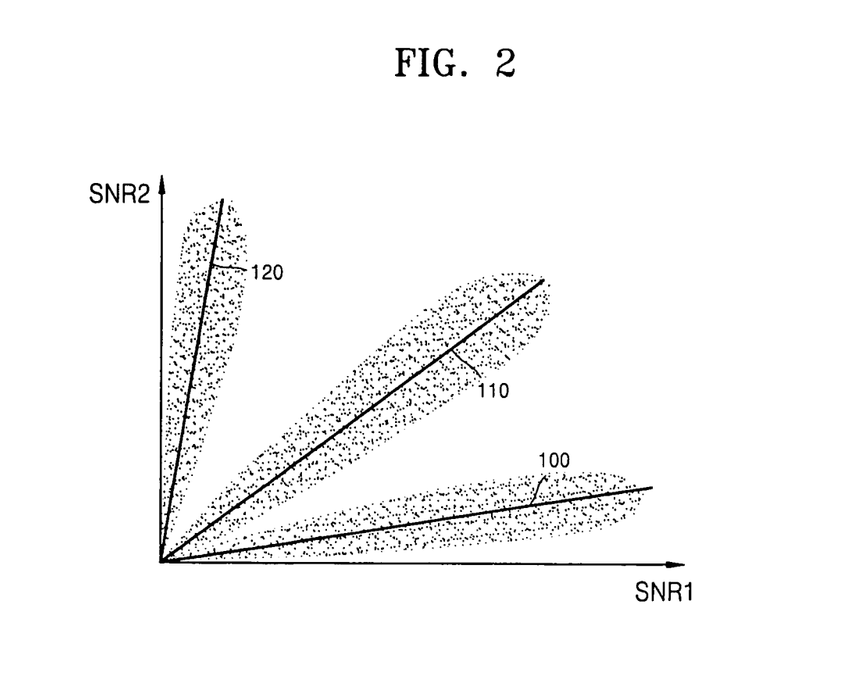
FIG. 2 is another graph illustrating genotype data plotted in a two-dimensional space.

FIG. 2 is another graph illustrating genotype data plotted in a two-dimensional space. In theory, the ratio of SNR1 to SNR2 should be constant for each genotype and, when the genotype data are plotted in the two-dimensional space, the genotype data should be plotted on straight lines having different gradients, as illustrated in FIG. 1. However, when SNR1 and SNR2 of the genotype data determined by experiment are calculated and plotted in the two-dimensional space, points representing the determined genotype data are located around straight lines 100, 110, and 120 as illustrated in FIG. 2.

Figure 3:
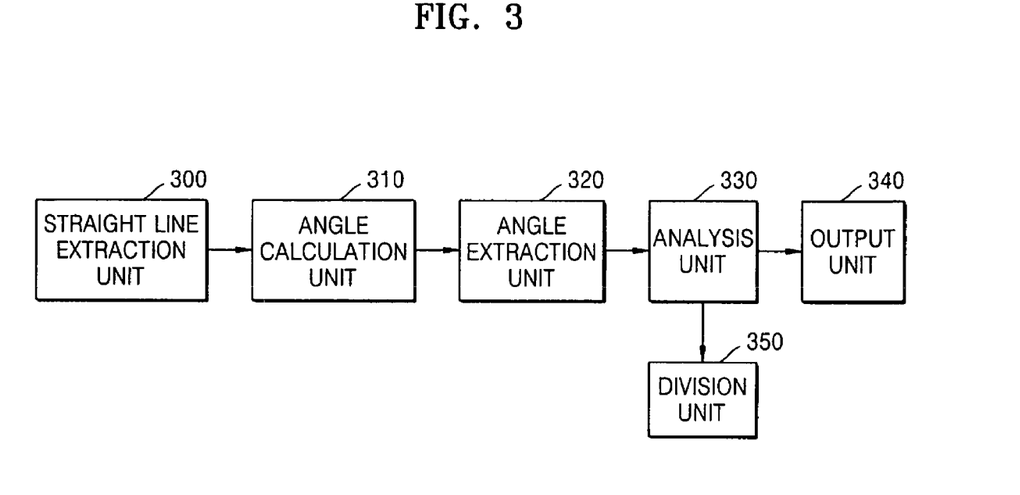
FIG. 3 is a block diagram of an apparatus for analyzing genotype data according to an embodiment of the present invention.

FIG. 3 is a block diagram of an apparatus for analyzing genotype data according to an embodiment of the present invention. Referring to FIG. 3, the apparatus comprises a straight line extraction unit 300, an angle calculation unit 310, an angle extraction unit 320, an analysis unit 330, an output unit 340, and a division unit 350. The operation of the apparatus illustrated in FIG. 3 will now be explained in connection with a method of analyzing genotype data according to an embodiment of the present invention illustrated in FIG. 9.

Figure 9:
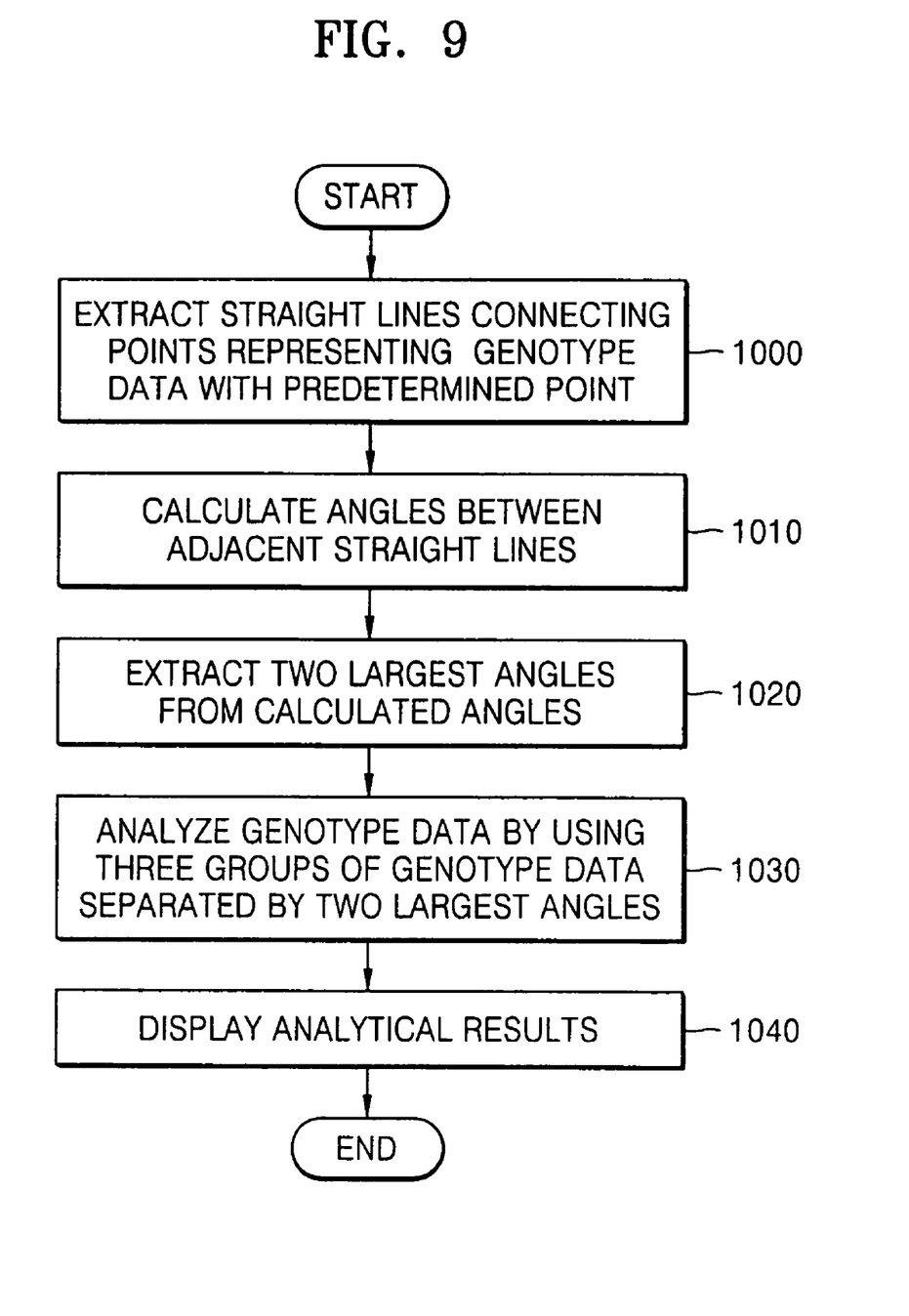
FIG. 9 is a flow chart illustrating a method of analyzing genotype data according to an embodiment of the present invention.

The straight line extraction unit 300 extracts straight lines connecting points representing the genotype data with a predetermined point in the two-dimensional space (operation 1000). The predetermined point may be the origin of a two-dimensional graph. Files in an image file format, such as GIF, may be input to the straight line extraction unit 300.

Figure 4:
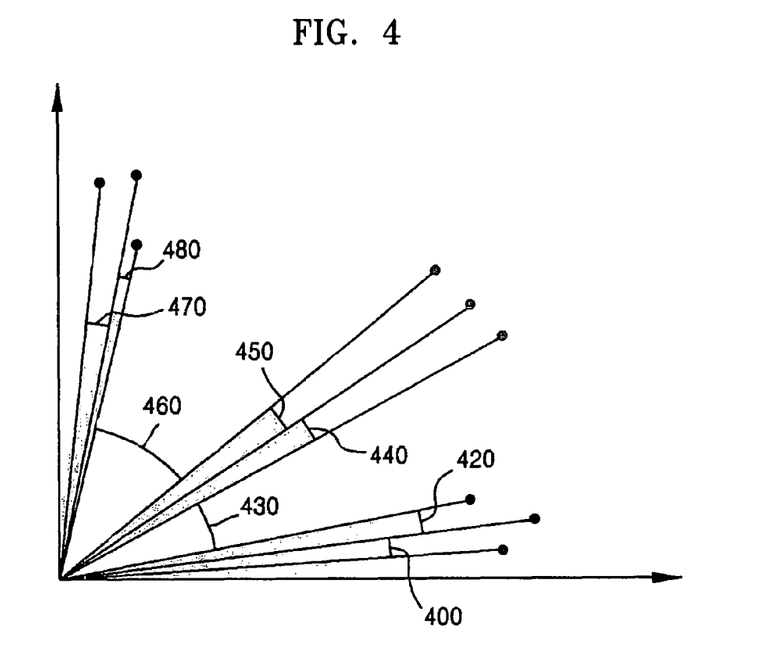
FIG. 4 is a graph illustrating an operation in which an angle calculation unit illustrated in FIG. 3 calculates angles between adjacent straight lines.

The angle calculation unit 310 calculates angles between adjacent straight lines extracted from the genotype data (operation 1010). FIG. 4 is a graph illustrating the operation of calculating angles between the adjacent straight lines extracted from the genotype data. Referring to FIG. 4, data related to homozygote 1 expressed by A1A1 are represented by red points, data related to heterozygote expressed by A1A2 are represented by green points, and data related to homozygote 2 expressed by A2A2 are represented by blue points. The straight line extraction unit 300 extracts straight lines connecting points representing the genotype data to the origin and the angle calculation unit 310 calculates angles 400, 420, 430, 440, 450, 460, 470, and 480 between the adjacent straight lines.

Figure 5:
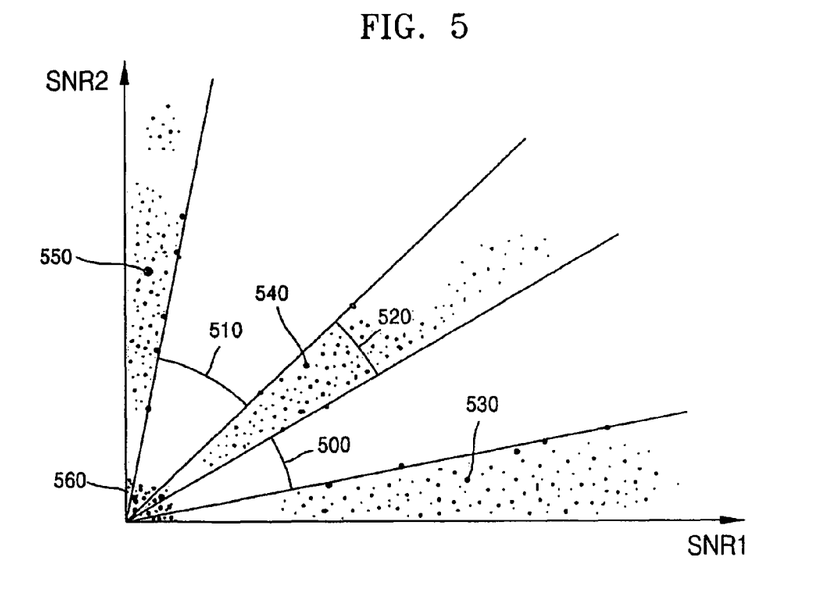
FIG. 5 is a graph illustrating an operation in which an angle extraction unit extracts the two largest angles.

All the angles between the adjacent straight lines from the angle calculation unit 310 are input to the angle extraction unit 320, and the angle extraction unit 320 extracts the two largest angles from the input angles (operation 1020). FIG. 5 is a graph illustrating the operation in which the angle extraction unit 320 extracts the two largest angles 500 and 510 from the obtained angles. Referring to FIG. 5, the genotype data are separated into three groups by the two largest extracted largest angles 500 and 510. The genotype data 530 located between the SNR1 axis and the first angle 500 correspond to A1A1, genotype data 540 located between the first angle 500 and the second angle 510 correspond to A1A2, and genotype data 550 located between the SNR2 axis and the second angle 510 correspond to A2A2. Genotype data 560 represented by black points are those for which the genotype are not classified.

The analysis unit 330 analyzes the experimental results of classifying the genotype data using the three groups of the genotype data separated by the two extracted largest angles (operation 1030).

Figure 6:
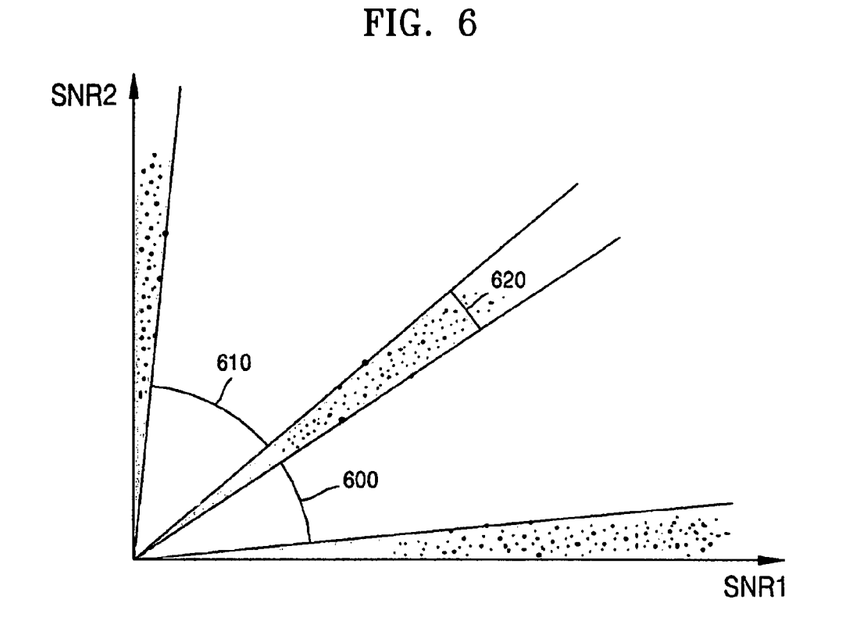
FIG. 6 is a graph of the results of analyzing the genotype data according to an embodiment of the present invention.
Figure 7:
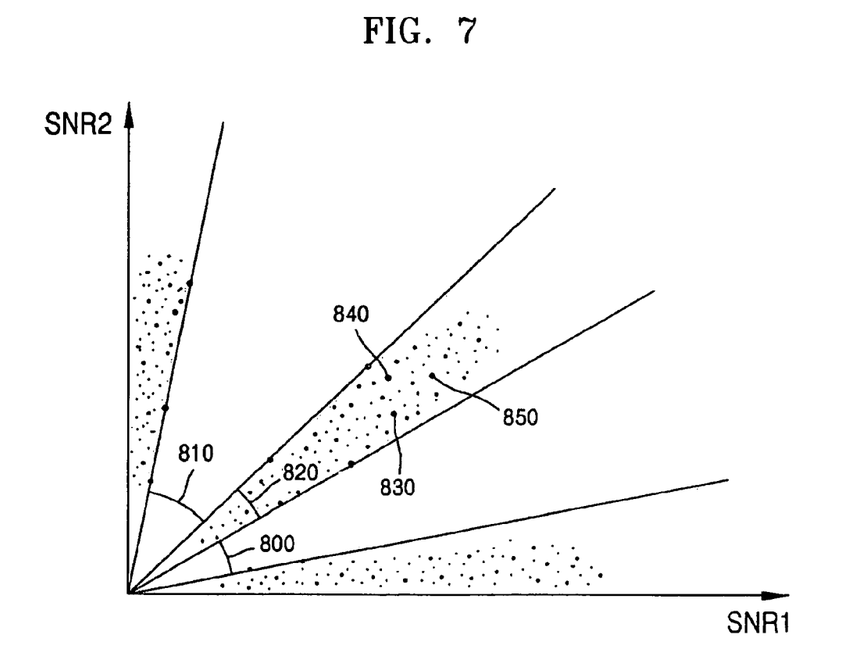
FIG. 7 is a graph of the results of analyzing the genotype data according to another embodiment of the present invention.
Figure 8:
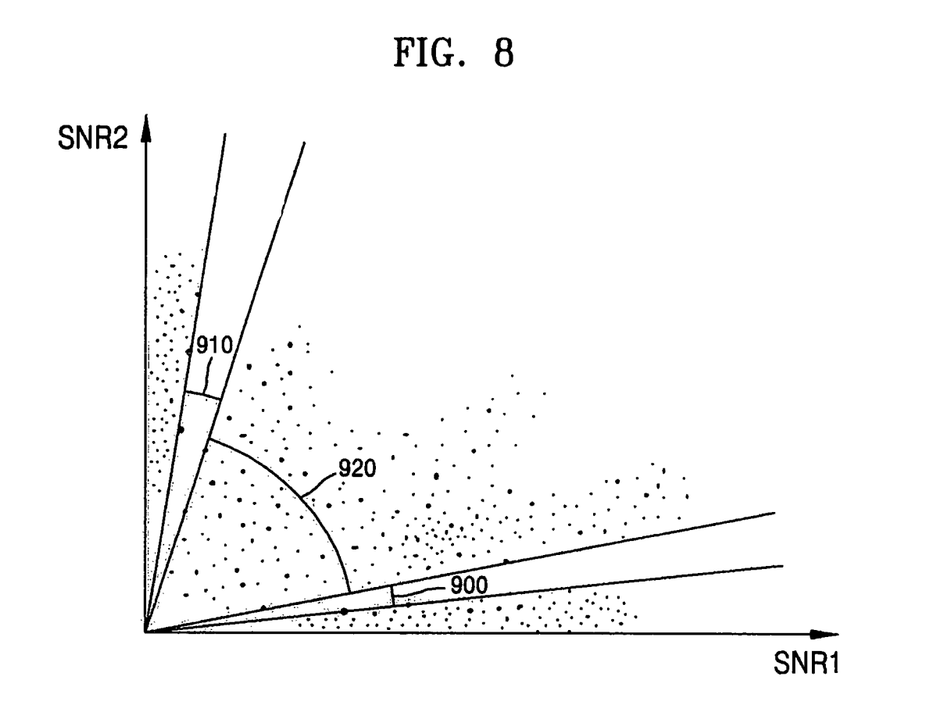
FIG. 8 is a graph of the results of analyzing the genotype data according to still another embodiment of the present invention.

Referring to FIGS. 6 through 8, the operation of analyzing the genotype data using the extracted largest angles will now be explained.

FIG. 6 is a graph of the results of analyzing the genotype data according to an embodiment of the present invention. Referring to FIG. 6, the two extracted largest angles 600 and 610 extracted by the angle extraction unit 320 are greater than a predetermined angle, for example, 20°, and the colors of all the points with each of the three regions separated by the two extracted largest angles 600 and 610 are identical. In this case, it is judged that the genotypes of the genotype data are classified in a good manner, and thus, the experimental results are reliable.

FIG. 7 is a graph of the results of analyzing the genotype data according to another embodiment of the present invention. Referring to FIG. 7, the two extracted largest angles 800 and 810 extracted by the angle extraction unit 320 are greater than a predetermined angle, for example, 20°, but the colors of all the points contained in each of the three regions separated by the two extracted largest angles 800 and 810 are not identical. Only the heterozygote expressed by A1A2 should be plotted in a region interposed between the two extracted largest angles 800 and 810, but three points 830, 840, and 850 classified as homozygote 1 expressed by A1A1 are plotted in the region interposed between the two extracted largest angles 800 and 810. In this case, it is judged that the genotypes of the genotype data are classified in a relatively good manner, but a review of the experiment for determining genotype data is required.

FIG. 8 is a graph of the results of analyzing the genotype data according to still another embodiment of the present invention. Referring to FIG. 8, the two extracted largest angles 900 and 910 extracted by the angle extraction unit 320 are less than a predetermined angle, for example, 20°. In this case, it is judged that the genotypes of the genotype data are not classified in a good manner, and thus, the experiment for determining the genotype data should be repeated. Alternatively, if a central angle 920 between the two extracted largest angles 900 and 910 is greater than a predetermined angle, for example, 40°, as illustrated in FIG. 8, it is judged that the genotypes of the genotype data are not classified in a good manner, and thus, the experiment for determining the genotype data should be repeated.

If the genotype data are represented by identical colors, for example, black, in a two-dimensional space, without being differentiated from each other based on genotype, the genotype data may be analyzed using the following operation.

If the two extracted largest angles extracted by the angle extraction unit 320 are greater than a predetermined angle, for example, 20°, it is judged that the genotypes of the genotype data are classified in a good manner, and thus, the experimental results are reliable. If the two extracted largest angles extracted by the angle extraction unit 320 are less than a predetermined angle, for example, 20°, and a central angle between the two extracted largest angles is less than a predetermined angle, for example, 40°, it is judged that the genotypes of the genotype data are classified in a relatively good manner, but a review of the experiment of determining genotype data is required. If the two extracted largest angles extracted by the angle extraction unit 320 are less than a predetermined angle, for example, 20°, and the central angle between the two extracted largest angles is greater than a predetermined angle, for example, 40°, it is judged that the genotypes of the genotype data are not classified in a good manner, and thus, the experiment for determining the genotype data should be repeated.

The predetermined angles used to analyze the genotype data may also be angles other than 20° and 40°.

The operation of analyzing the genotype data may further comprise detecting the distribution and number of genotype data which are not classified into the three genotypes, for example, the black points illustrated in FIG. 5, and, if the black points are located more than a predetermined distance from the origin, judging that the genotypes of the genotype data are not classified in a good manner, and thus, the experiment for determining the genotype data should be repeated.

The results of analyzing the genotype data are input to the output unit 340 from the analysis unit 330, and the output unit 340 displays the analytical results on a screen or prints them on paper such that a user can confirm the analytical results with the naked eye (operation 1040).

The results of analyzing the genotype data are input to the division unit 350 from the analysis unit 330 and if reclassification of the genotypes of the genotype data is required, the division unit 350 reclassifies the genotype according to the analytical results. For example, when the three points 830, 840, and 850 have different colors from the color of the region in which they are contained, the region being one of the three regions separated by the angles 800 and 810, as illustrated in FIG. 7, the genotypes of the genotype data corresponding to the points 830, 840, and 850 may be reclassified such that the colors of the points 830, 840, and 850 are identical to the colors of the regions in which they are contained. In the case of FIG. 7, the genotype data corresponding to the points 830, 840, and 850 are reclassified as A1A2.

The invention can also be embodied as computer readable code on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices. Also, functional programs, code, and code segments for accomplishing the present invention can be easily construed by programmers skilled in the art to which the present invention pertains.

According to a method and apparatus for analyzing genotype data in embodiments of the present invention, the two largest angles obtained by connecting points representing genotype data to a predetermined point plotted in a two-dimensional space with straight lines are detected, and three data regions separated by the detected two angles are used to analyze the genotype data. Thus, a large amount of the experimental data for classifying genotypes can be analyzed rapidly and conveniently.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of analyzing reliability of genotype data at a plurality of different biallelic polymorphic sites, comprising:

connecting points representing genotype data plotted in each of a plurality of two-dimensional graphs to the origin of the two-dimensional graph to form straight lines, wherein a first axis of each two dimensional graph represents a first signal-to-noise ratio (SNR1) of experimental data indicating A1 of the genotype and the second axis of each two dimensional graph represents a second signal-to-noise ratio (SNR2) of experimental data indicating A2 of the genotype, wherein each graph contains points representing genotype data for a single biallelic polymorphic site selected from a plurality of different biallelic polymorphic sites;

obtaining angles between adjacent straight lines;

extracting the two largest angles from the obtained angles;

classifying the genotype data for each graph into three genotype groups separated by the two extracted largest angles, wherein the three genotype groups are A1A1, A1A2, and A2A2; and analyzing the reliability of the classified results of each of the graphs using the three groups of the genotype data separated by the two extracted largest angles such that for each graph if at least one of the two extracted largest angles is less than a first predetermined angle or if an angle of the center group among the three groups is greater than a second predetermined angle, judging that genotype classification of the graph is incorrect;

if the two extracted largest angles are greater than the first predetermined angle, judging that genotype classification of the graph is correct; or if the two extracted largest angles are less than the first predetermined angle and the angle of the center group among the three groups is less than the second predetermined angle, judging that genotype classification of the graph is correct, but that a review of the experiment of determining the genotype data of the graphs is required; and wherein the steps of the method are executed on a suitably programmed computer.

2. The method of claim 1, wherein the obtaining of the angles between the adjacent straight lines comprises:

obtaining angles between the straight lines and a predetermined straight line and arranging the obtained angles in a decreasing order; and calculating differences between the adjacent angles.

3. The method of claim 1, wherein the genotype data plotted in the two-dimensional space is represented with different colors according to the genotype represented.

4. The method of claim 3, further comprising:

detecting the genotype data in each of the groups represented with a color other than the color representing the genotype data associated with the group;

obtaining the coordinates and number of the detected genotype data; and analyzing the detected genotype data by using the coordinates and number of the detected genotype data.

5. The method of claim 3, wherein the analyzing the reliability of the classified results of each of the graphs comprises:

if at least one of the two extracted largest angles is less than a first predetermined angle, judging that the experiment for determining the genotype data should be repeated;

if the two extracted largest angles are greater than the first predetermined angle and the colors of the genotype data contained in each of the groups are identical, judging that genotype classification of the plotted genotype data is correct; and if the two extracted largest angles are greater than the first predetermined angle and the colors of the genotype data contained in each of the groups are different from each other, judging that a review of the experiment of determining the genotype data is required.

6. The method of claim 5, further comprising reclassifying the genotype of the genotype data using the results of analyzing the reliability of the classified results of each of the graphs.

7. A computer-readable recording medium having recorded thereon a program for executing the method of claim 1 in a computer.

8. The method of claim 1, wherein the first predetermined angle is 20 degrees.

9. The method of claim 1, wherein the second predetermined angle is 40 degrees.

* * * * *